United States Patent [19]

Hainaut et al.

[11] 4,043,796
[45] Aug. 23, 1977

[54] SELECTIVE HERBICIDAL COMPOSITIONS

[75] Inventors: Daniel Hainaut, Villemomble; Jean-Pierre Demoute, Montreuil-sous-Bois; Andre Teche, Nanterre, all of France

[73] Assignee: Roussel Uclaf, Paris, France

[21] Appl. No.: 658,331

[22] Filed: Feb. 17, 1976

[30] Foreign Application Priority Data

Feb. 18, 1975 France .................................. 75.04978
Nov. 28, 1975 France .................................. 75.36459

[51] Int. Cl.$^2$ ...................... A01N 9/12; C07C 119/00
[52] U.S. Cl. ............................................. 71/98; 71/103; 260/453 RW
[58] Field of Search ..................... 260/453 RW; 71/98

[56] References Cited

U.S. PATENT DOCUMENTS

| 3,326,663 | 6/1967 | Soloway et al. | 260/453 R |
| 3,697,572 | 10/1972 | Brown | 260/453 R |
| 3,812,209 | 5/1974 | Brown | 260/453 R |
| 3,857,883 | 12/1974 | Cleveland | 71/98 |
| 3,946,062 | 3/1976 | Cleveland | 71/98 |

OTHER PUBLICATIONS

Chimetron, "Herbicidal n-(haloalkylthio) etc.," (1966) CA69 No. 96303z. (1968).

Primary Examiner—Glennon H. Hollrah
Attorney, Agent, or Firm—Hammond & Littell

[57] ABSTRACT

Novel selective herbicidal compositions comprising an herbicidally effective amount of at least one compound selected from the group consisting of N-methyl-N-isopropylthio-N'-phenyl-urea, N-methyl-N-(2-chloroethylthio)-N'-(3,4-dichlorophenyl)-urea, N-methyl-N-n-butylthio-N'-(4-isopropylphenyl)-urea, N-methyl-N-isopropylthio-N'-(4-isopropylphenyl)-urea, N-methyl-N-isopropylthio-N'-(3,4-dimethylphenyl)-urea and N-methyl-N-n-butylthio-N'-(3,4-dimethylphenyl)-urea and a carrier and a method of selectively killing weeds in cereal crops and fields of beets.

8 Claims, No Drawings

SELECTIVE HERBICIDAL COMPOSITIONS

STATE OF THE ART

French Pat. No. 2,065,315 describes the use of N-(2-fluorophenyl)-N'-substituted ureas as herbicides and West German published application Ser. No. 1,910,490 describes the use of N-aryl-N'-alkyl-N'-arylthio-ureas as herbicides. U.S. Pat. Nos. 3,165,549, 3,288,586 and No. 3,228,762 also disclosed various urea compounds as herbicides and Danish Pat. Nos. 115,159 and 117,872 and German Pat. No. 1,204,879 described N-phenyl-N'-alkyl ureas as herbicides. Published Japanese application No. 35035/1973 also describes phenyl ureas as herbicides.

Our copending, commonly assigned U.S. Pat. application Ser. No. 615,401 filed Sept. 22, 1975 discloses generically urea derivatives of the formula

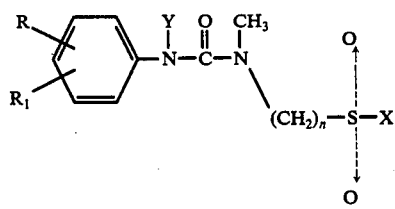

I wherein R and $R_1$ are individually selected from the group consisting of hydrogen, chlorine, bromine, nitro, trifluoromethyl, lower alkyl of 1 to 6 carbon atoms and lower alkoxy of 1 to 6 carbon atoms, $n$ is 0 or 1, X is selected from the group consisting of lower alkyl of 1 to 6 carbon atoms optionally substituted with halogen and a nitrogen heterocyclic optionally containing 1 or more other heteroatoms, Y is selected from the group consisting of hydrogen, alkyl of 1 to 4 carbon atoms and S-Z wherein Z is a nitrogen heterocyclic optionally containing 1 or more other heteroatoms and the dotted lines indicate that the compounds of formula I may contain no oxygen bound to the sulfur atom or may be in sulfoxide or sulfonyl form which are useful as herbicides.

OBJECTS OF THE INVENTION

It is an object of the invention to provide novel substituted ureas and their preparation.

It is another object of the invention to provide novel herbicidal compositions.

It is a further object of the invention to provide a novel method of killing weeds, particularly in cereal crops and fields of beets. These and other objects and advantages of the invention will become obvious from the following detailed description.

THE INVENTION

The novel selective herbicidal compositions of the invention are comprised of an herbicidally effective amount of at least one compound selected from the group consisting of N-methyl-N-isopropylthio-N'-phenyl-urea, N-methyl-N-(2-chloroethylthio)-N'-(3,4-dichlorophenyl)-urea, N-methyl-N-n-butylthio-N'-(4-isopropylphenyl)-urea, N-methyl-N-isopropylthio-N'-(3,4-dimethylphenyl)-urea, N-methyl-N-n-butylthio-N'-(3,4-dimethylphenyl)-urea and a carrier. The compositions may also contain one or more other pesticides or one or more other products to influence the growth of plants.

The said compositions may be in the form of powders, granules, suspensions, emulsions or solution containing the active ingredient such as a mixture with a vehicle and/or an anionic, cationic or nonionic surface active agent assuring, with others, a uniform dispersion of the substances of the composition. The vehicle used may be a liquid such as water, alcohol, hydrocarbons or other organic solvents, animal, vegetable or mineral oils or a powder such as talc, clays, silicates or kieselguhr. The compositions generally contain 5 to 90%, preferably 10 to 50% by weight of the active ingredient.

The remarkable herbicidal properties of the compounds of formula I make them useful in agriculture for combatting harmful organisms and particularly undesired weeds. The herbicidal properties have been demonstrated by tests on plants or large botanical families are reported herein.

The novel method of the invention of combatting weeds comprises contacting the weeds either pre-emergence or post-emergence with a herbicidally effective amount of at least one compound of formula I.

The ureas may be prepared by the process described in our copending application Ser. No. 615,401 by reacting the desired N-methyl-N'-phenyl-urea in the presence of a tertiary amine with a chloride of the formula

wherein X is n-butyl, isopropyl or 2-chloroethyl to obtain the corresponding desired urea. The preferred tertiary base is pyridine or triethylamine.

In the following examples there are described several preferred embodiments to illustrate the invention. However, it should be understood that the invention is not intended to be limited to the specific embodiments.

EXAMPLE 1

N-methyl-N-isopropylthio-N'-phenyl-urea 27 g of chlorosulfuric acid were slowly added at −30° C to a mixture of 30 g of diisopropyl disulfide and 200 ml of methylene chloride and after the temperature returned to 10° C, the mixture was stirred at 10° C for 15 minutes to obtain a solution of isopropyl sulfenyl chloride to which was slowly added at −30° C a solution of 30 g of N-methyl-N'-phenyl-urea in 280 ml of pyridine. The temperature was allowed to raise to 0° C and the mixture was then stirred for 2 hours at 0° C and was poured into a mixture of water, ice, hydrochloric acid and methylene chloride. The organic phase was decanted, dried and evaporated to dryness under reduced pressure and the residue was chromatographed over silica gel. Elution was effected with a 9-1 benzene-ethyl acetate mixture and the product was dissolved in isopropyl ether. The solution was iced to −80° C to obtain 23 g of N-methyl-N-isopropylthio-N'-phenyl urea melting at ' 50° C.

Analysis: $C_{11}H_{16}N_2OS$ Calculated: %C 58.91, %H 7.19; %N 12.49; %S 14.30; Found: %C 59.2; %H 7.3; %N b 12.6; %S 14.3.

EXAMPLE 2

N-(2-chloroethylthio)-N-methyl-N'-(3,4-dichlorophenyl)-urea 27 g of chlorosulfuric acid were slowly added at 0° C to a mixture of 12 g of ethylene sulfide and 200 ml of methylene chloride and the mixture was stirred at 0° C for 10 minutes and was then cooled to −20° C. A mixture of 32.6 g of N-methyl-N'-(3,4-dichlorophenyl)-urea in 210 ml of pyridine was added to the reaction mixture after which the temperature returned to 0° C. The mixture was stirred at 0° C for 10 minutes and was then poured into a mixture of ice, water, hydrochloric acid and methylene chloride. The mixture was stirred for 30 minutes and the decanted organic phase was washed, dried, filtered and concentrated to dryness under reduced pressure. The residue was chromatographed over silica gel and the product was eluted witn 9-1 benzene-ethyl acetate mixture and was crystallized from isopropyl ether to obtain 10 g of N-(2-chloroethylthio)-N-methyl-N'-(3,4-dichlorophenyl)-urea melting at 62° C.

Analysis: $C_{10}H_{11}Cl_3N_2OS$ Calculated: %C 38.29; %H 3.54; %N 8.93; %Cl 33.92; %S 10.22; Found: %C 38.3; %H 3.6; %N 8.7; %Cl 33.8; %S 10.0

EXAMPLE 3

N-methyl-N-n-butylthio-N'-(4-isopropylphenyl)-urea 16 ml of chlorosulfuric acid were added at −25° C to a mixture of 35.6 g of di-n-butyl disulfide in 200 ml of methylene chloride and the mixture was stirred at −5° C and was then cooled to −40° C. A mixture of 38.5 g of N-methyl-N'-(4-isopropylphenyl)-urea in 280 ml of pyridine was added dropwise to the mixture which was then stirred and poured into a mixture of water, hydrochloric acid and methylene chloride. The decanted organic phase was dired and concentrated to dryness and the residue was chromatographed over silica gel. Elution with a 95-5 benzene-ethyl acetate mixture yielded 15.5 g of a clear yellow oil which was N-methyl-N-n-butylthio-N'-(4-isopropylphenyl)-urea.

Analysis: $C_{15}H_{24}N_2OS$ Calculated: %C 64.25; %H 8.63; %N 9.99; %S 11.43; Found: %C 64.5; %H 8.9; %N 9.7; %S 11.4.

EXAMPLE 4

N-methyl-N-isopropylthio-N'-(4-isopropylphenyl)-urea 16 ml of chlorosulfuric acid were added dropwise at −25° C to a mixture of 30 g of diisopropyl disulfide in 200 ml of methylene chloride and the mixture was stirred at −5° C and then was cooled at −30° C. A mixture of 38.5 g of N-methyl-N'-(4-isopropylphenyl)-urea in 280 ml of pyridine was added to the reaction mixture which was then stirred at −15° C for one hour and was then poured into a water, ice, hydrochloric acid and methylene chloride mixture. The decanted organic phase was dried and evaporated to dryness and the residue was chromatographed over silica gel. Elution with a 95-5 benzeneethyl acetate mixture yielded 29 g of N-methyl-N-isopropylthio -N'-(4-isopropylphenyl)-urea in the form of a yellow oil.

Analysis: $C_{14}H_{22}N_2OS$ Calculated: %C 63.12; %H 8.32; %N 10.52; %S 12.04; Found: %C 63.4; %H 8.4; %N 10.1; %S 11.8

EXAMPLE 5

N-methyl-N-isopropylthio-N'-(3,4-dimethylphenyl)-urea

Using the procedure of Example 4, N-methyl-N'-(3,4-dimethylphenyl)-urea was reacted to obtain 28 g of N-methyl-N-isopropylthio-N'-(3,4-dimethylphenyl)-urea.

Analysis: $C_{13}H_{20}N_2OS$ Calculated: %C 61.87; %H 7.99; %N 11.1; %S 12.7; Found: %C 62.1; %H 8.0; %N 10.6; %S 12.3.

EXAMPLE 6

N-methyl-N-n-butylthio-N'-(3,4-dimethylphenyl)-urea 16 ml of chlorosulfuric acid were added at −25° C to a mixture of 35.6 g. of di-n-butyl disulfide in 200 ml of methylene chloride and the mixture was stirred at −5° C and then was cooled to −40° C. A mixture of 35.6 g of N-methyl-N'-(3,4-dimethylphenyl)-urea in 280 ml of pyridine was added to the reaction mixture and the mixture was then stirred into a water, ice, hydrochloric acid and methylene chloride mixture. The decanted organic phase was dired and evaporated to dryness and the residue was chromatographed over silica gel. Elution with a 9-1 benzene-ethyl acetate mixture yielded 20 g of N-methyl-N-n-butylthio-N'-(3,4-dimethylphenyl)-urea in the form of a yellow oil.

Analysis: $C_{14}H_{22}N_2OS$ Calculated: %C 63.12; %H 8.32; %N 10.51; %S 12.04; Found: %C 63.1; %H 8.1; %N 10.0; %S 11.8.

HERBICIDAL COMPOSITIONS

Herbicidal compositions in the form of a wettable powder were prepared containing 25% by weight of N-methyl-N-isopropylthio-N'-phenyl-urea or N-methyl-N-n-butylthio-N'-(4-isopropylphenyl)-urea, 15% by weight of Ekapersol S (condensation product of sodium naphthalene sulfonate), 0.5% by weight of Brecolane NVA (sodium alkyl naphthalene sulfonate) 34.5% by weight of Zerosil 39 (precipitated synthetic hydrated silica) and 25% by weight of Vercoryl S (colloidal Kaolin).

HERBICIDAL ACTIVITY

The test plants were grown in a culture flat (23 × 14 × 4 cm) having a double bottom and means for watering from below. The species were placed into a single flat at a ratio of 20 seeds per species, in rows spaced 3 cm apart. There were four sets of flats for each compound and concentration. The growing conditions were: temperature 20° C " 2° C, humidity about 60%, lighting by a fluoescent tube (day light + brilliant white) from 6 hours to 22 hours each day. The soil mixture was composed of 10 volumes of earth, 10 volumes of river sand and 2 volumes of peat.

For the pre-emergence tests, the herbicidal treatment was carried out 24 hours after the seeds had been planted and the first watering was effected by sprinkling to carry a part of the product to the seed level. The post-emergence tests were effected by 21 days after the seeds had been planted, on the aerial parts. The test products were each applied under standard conditions with the aid of a microsprayer at doses of 10, 5, 2.5, 1.25, 0.625, 0.312 and 0.156 kg/ha and at a dilution of 560 1/ha. Control tests without treatment were carried out in the same way. The final controls were effected by weight of the plants 21 days after treatment in the pre-emergence test and 15 days after treatment in the post-emergence test. The results where expressed as a percentage of reduction of weight of the vegatation P $$P = \frac{\text{weight of control plants} - \text{weight of treated plants}}{\text{weight of control plants}} \times 100$$

TABLE 1

N-methyl-N-isopropylthio-N'-phenyl-urea

| Concentrations in Kg/ ha products | Pre-Emergence | | | | Post-Emergence | | | |
|---|---|---|---|---|---|---|---|---|
| | 5.0 | 2.5 | 1.25 | 0.625 | 5.0 | 2.5 | 1.25 | 0.625 |
| Bent Grass | 100 | 100 | 100 | 0 | 100 | 100 | 100 | 92 |
| Oats | 71 | 57 | 28 | 42 | 60 | 37 | 28 | 0 |
| Wheat | 60 | 48 | 29 | 0 | 52 | 42 | 26 | 25 |
| Corn | 41 | 22 | 0 | 0 | 27 | 0 | 0 | 0 |
| Barley | 78 | 36 | 41 | 22 | 50 | 48 | 0 | 0 |
| Rye-Grass | 100 | 84 | 65 | 67 | 100 | 74 | 60 | 40 |
| Beets | 100 | 100 | 97 | 76 | 100 | 100 | 100 | 79 |
| Chenopode | 100 | 100 | 100 | 100 | 100 | 100 | 100 | 100 |
| Chrysanthemum | 100 | 100 | 100 | 29 | 100 | 100 | 69 | 43 |
| Mustard | 100 | 100 | 100 | 96 | 100 | 100 | 96 | 74 |
| Rumex | 100 | 100 | 100 | 92 | 100 | 100 | 98 | 88 |
| Clover | 100 | 100 | 100 | 100 | 100 | 100 | 100 | 100 |

TABLE 2

N-methyl-N-(2-chloroethylthio)-N'-(3,4-dichlorophenyl)-urea

| Concentrations in Kg/ha products | Pre-Emergence | | | | | |
|---|---|---|---|---|---|---|
| | 5.0 | 2.5 | 1.25 | 0.625 | 0.312 | 0.156 |
| Bent Grass | 88 | 80 | 69 | 0 | | |
| Oats | 89 | 72 | 45 | 20 | | |
| Wheat | 89 | 49 | 0 | 0 | | |
| Corn | 0 | 0 | 0 | 0 | | |
| Barley | 86 | 56 | 0 | 0 | | |
| Rye-Grass | 100 | 100 | 91 | 71 | | |
| Beets | 100 | 100 | 100 | 83 | 43 | 40 |
| Chenopode | 100 | 100 | 100 | 100 | 0 | 0 |
| Chrysanthemum | 100 | 100 | 100 | 98 | 34 | 20 |
| Gaillet | — | — | — | — | — | — |
| Mustard | 100 | 100 | 100 | 100 | 95 | 33 |
| Rumex | 100 | 100 | 100 | 100 | 80 | 37 |
| Clover | 100 | 100 | 100 | 100 | 72 | 55 |

TABLE 3

N-methyl-N-(2-chloroethylthio)-N'-(3,4-dichlorophenyl)-urea

| Concentrations in Kg/ha products | Post-Emergence | | | | | |
|---|---|---|---|---|---|---|
| | 5.0 | 2.5 | 1.25 | 0.625 | 0.312 | 0.156 |
| Bent Grass | 100 | 100 | 100 | 100 | 83 | 33 |
| Oats | 100 | 100 | 100 | 74 | 0 | 0 |
| Wheat | 100 | 93 | 85 | 72 | 26 | 27 |
| Corn | 86 | 75 | 36 | 0 | 0 | 0 |
| Barley | 100 | 96 | 97 | 81 | 0 | 0 |
| Rye-Grass | 100 | 100 | 100 | 100 | 80 | 68 |
| Beets | 100 | 100 | 100 | 100 | 100 | 100 |
| Chenopode | 100 | 100 | 100 | 100 | 100 | 100 |
| Chrysanthemum | 100 | 100 | 100 | 100 | 100 | 100 |
| Gaillet | 100 | 100 | 100 | 100 | 100 | — |
| Mustard | 100 | 100 | 100 | 100 | 100 | 100 |
| Rumex | 100 | 100 | 100 | 100 | 100 | 100 |
| Clover | 100 | 100 | 100 | 100 | 100 | 100 |

HERBICIDAL ACTIVITY

The test plants were grown in a culture flat (23 × 14 × 4 cm) having a double bottom and means for watering from below. The species were placed into a single flat at a ratio of 20 seeds per species, in rows spaced 3 cm apart. There were four sets or flats for each compound and concentration. The growing conditions were: temperatue 20° C ± 2° C, humidity about 60%, lighting by a fluorescent tube (day light + birlliant white) from 6 hours to 22 hours each day. The soil mixture was composed of 10 volumes of earth, 10 volumes of river sand and 2 volumes of peat.

For the pre-emergence tests, the herbicidal treatment was carried out 24 hours after the seeds has been planted and the first watering was effected by sprinkling to carry a part of the product to the seed level. The post-emergence tests were effected by 21 days after the seeds had been planted, on the aerial part. The test products were each applied under standard conditions with the aid of a microsprayer at doses of 10, 5, 2.5, 1.25, 0.625, 0.312 and 0.156 kg/ha and at a dilution of 560 l/ha. Control tests without treatment were carried out in the same way. The final controls were effected by counting the plants 21 days after treatment in the pre-emergence test and 15 days after treatment in the post-emergence test. The results were expressed as a percentage of mortality M.

$$M = \frac{\text{Number of control plants} - \text{Number of still living treated plants}}{\text{Number of control plants}} \times 100$$

TABLE 4

N-methyl-N-n-butylthio-N'-(4-isopropylphenyl)-urea

| Concentrations in Kg/ ha products | Pre-Emergence | | | | Post-Emergence | | | |
|---|---|---|---|---|---|---|---|---|
| | 5.0 | 2.5 | 1.25 | 0.625 | 5.0 | 2.5 | 1.25 | 0.625 |
| Bent Grass | 92 | 77 | 49 | 0 | 100 | 100 | 81 | 47 |
| Oats | 65 | 0 | 0 | 0 | 81 | 0 | 0 | 0 |
| Wheat | 0 | 0 | 0 | 0 | 0 | 0 | 0 | 0 |
| Corn | 0 | 0 | 0 | 0 | 11 | 0 | 0 | 0 |
| Barley | 0 | 0 | 0 | 0 | 0 | 0 | 0 | 0 |
| Rye-Grass | 100 | 44 | 0 | 0 | 59 | 76 | 55 | 0 |
| Beets | 100 | 100 | 85 | 40 | 100 | 100 | 100 | 43 |
| Chenopode | 100 | 100 | 100 | 63 | 100 | 100 | 100 | 100 |
| Chrysanthemum | 100 | 100 | 100 | 77 | 100 | 100 | 100 | 67 |
| Gaillet | 52 | 33 | 0 | 0 | 100 | 78 | 37 | 0 |
| Mustard | 100 | 100 | 100 | 58 | 100 | 86 | 68 | 0 |
| Rumex | 100 | 100 | 88 | 20 | 100 | 100 | 100 | 80 |
| Clover | 100 | 100 | 100 | 79 | 100 | 100 | 82 | 44 |

TABLE 5

N-methyl-N-isopropylthio-N'-(4-isopropylphenyl)-urea

| Concentrations in Kg/ha products | Pre-Emergence | | | |
|---|---|---|---|---|
| | 5.0 | 2.5 | 1.25 | 0.625 |
| Bent Grass | 81 | 0 | 0 | 0 |
| Oats | 100 | 85 | 0 | 0 |
| Wheat | 0 | 0 | 0 | 0 |
| Corn | 0 | 0 | 0 | 0 |
| Barley | 13 | 0 | 0 | 0 |
| Rye-Grass | 100 | 89 | 47 | 36 |
| Beets | 100 | 100 | 100 | 85 |
| Chenopode | 100 | 100 | 100 | 100 |
| Chrysanthemum | 100 | 100 | 100 | 100 |
| Gaillet | 58 | 36 | 0 | 0 |
| Mustard | 100 | 100 | 100 | 100 |
| Rumex | 100 | 100 | 100 | 100 |
| Clover | 100 | 100 | 100 | 100 |

TABLE 6

N-methyl-N-isopropylthio-N'-(3,4-dimethylphenyl)-urea

| Concentrations in Kg/ ha products | Pre-Emergence | | | | Post-Emergence | | | |
|---|---|---|---|---|---|---|---|---|
| | 5.0 | 2.5 | 1.25 | 0.625 | 5.0 | 2.5 | 1.25 | 0.625 |
| Bent Grass | 0 | 0 | 0 | 0 | 100 | 100 | 92 | 53 |
| Oats | 0 | 0 | 0 | 0 | 100 | 0 | 0 | 0 |
| Wheat | 0 | 0 | 0 | 0 | 38 | 0 | 0 | 0 |
| Corn | 0 | 0 | 0 | 0 | 50 | 0 | 0 | 0 |
| Barley | 0 | 0 | 0 | 0 | 100 | 0 | 0 | 0 |
| Rye-Grass | 0 | 0 | 0 | 0 | 100 | 65 | 84 | 25 |
| Beets | 100 | 100 | 0 | 0 | 100 | 100 | 100 | 83 |
| Chenopode | 100 | 100 | 100 | 100 | 100 | 100 | 100 | 100 |
| Chrysanthemum | 100 | 100 | 100 | 56 | 100 | 100 | 94 | 88 |
| Gaillet | 17 | 0 | 0 | 0 | 100 | 42 | 0 | 0 |
| Mustard | 100 | 100 | 43 | 0 | 100 | 100 | 61 | 47 |
| Rumex | 100 | 100 | 0 | 0 | 100 | 100 | 95 | 0 |
| Clover | 100 | 100 | 100 | 0 | 100 | 100 | 100 | 58 |

TABLE 7

N-methyl-N-n-butylthio-N'-(3,4-dimethylphenyl)-urea

| Concentrations in Kg/ ha products | Pre-Emergence | | | | Post-Emergence | | | |
|---|---|---|---|---|---|---|---|---|
| | 5.0 | 2.5 | 1.25 | 0.625 | 5.0 | 2.5 | 1.25 | 0.625 |
| Bent Grass | 0 | 0 | 0 | 0 | 100 | 100 | 100 | 100 |
| Oats | 77 | 57 | 23 | 0 | 100 | 100 | 68 | 0 |
| Wheat | 0 | 0 | 0 | 0 | 28 | 0 | 0 | 0 |
| Corn | 0 | 0 | 0 | 0 | 47 | 0 | 0 | 0 |

TABLE 7-continued

N-methyl-N-n-butylthio-N'-(3,4-dimethylphenyl)-urea

| Concentrations in Kg/ha products | Pre-Emergence | | | | Post-Emergence | | | |
|---|---|---|---|---|---|---|---|---|
| | 5.0 | 2.5 | 1.25 | 0.625 | 5.0 | 2.5 | 1.25 | 0.625 |
| Barley | 0 | 0 | 0 | 0 | 34 | 0 | 0 | 0 |
| Rye-Grass | 100 | 36 | 0 | 0 | 100 | 100 | 100 | 100 |
| Beets | 100 | 100 | 32 | 0 | 100 | 100 | 100 | 91 |
| Chenopode | 100 | 100 | 100 | 100 | 100 | 100 | 100 | 100 |
| Chrysanthemum | 100 | 100 | 100 | 100 | 100 | 100 | 100 | 100 |
| Gaillet | 0 | 0 | 0 | 0 | 100 | 100 | 78 | 0 |
| Mustard | 100 | 100 | 100 | 65 | 100 | 100 | 100 | 82 |
| Rumex | 100 | 100 | 100 | 85 | 100 | 100 | 100 | 100 |
| Clover | 100 | 100 | 100 | 91 | 100 | 100 | 100 | 89 |

The results of Tables 1 to 7 show that the tested compounds have a good pre-and post-emergence herbicidal activity, particularly against dicotyledons. Moreover, this is not a general herbicidal activity but rather a selective activity with some of them presenting selective activity with respect to dicotyledons at certain doses, for example with respect to beets. The products at certain doses are only slightly active against graminaceous plants, particularly cultivated graminaceous plants permitting their selective use in cereal crops.

Various modifications of the compositions and method of the invention may be made without departing from the spirit or scope thereof and it should be understood that the invention is to be limited only as defined in the appended claims.

We claim:

1. A method of selectively killing weeds in cereal crops comprising applying to cereal crops an herbicidally effective amount of a compound selected from the group consisting of N-methyl-N-isopropylthio-N'-phenyl-urea, N-methyl-N-(2-chloroethylthio)-N'-(3,4-dichlorophenyl)-urea, N-methyl-N-n-butylthio-N'-(4-isopropylphenyl)-urea, N-methyl-N-isopropylthio-N'-(4-isopropylphenyl)-urea, N-methyl-N-isopropylthio-N'-(3,4-dimethylphenyl)-urea and N-methyl-N-n-butylthio-N'-(3,4-dimethylphenyl)-urea and an inert carrier.

2. A method of claim 1 wherein the compound is N-methyl-N-isopropylthio-N'-phenyl-urea.

3. A method of claim 1 wherein the compound is N-methyl-N-(2-chloroethylthio)-N'-(3,4-dichlorophenyl)-urea.

4. A method of claim 1 wherein the compound is N-methyl-N-n-butylthio-N'-(4-isopropylphenyl)-urea.

5. A method of claim 1 wherein the compound is N-methyl-N-isopropylthio-N'-(4-isopropylphenyl)-urea.

6. A method of claim 1 wherein the compound is N-methyl-N-isopropylthio-N'-(3,4-dimethylphenyl)-urea.

7. A method of claim 1 wherein the compound is N-methyl-N-n-butylthio-N'-(3,4-dimethylphenyl)-urea.

8. N-methyl-N-(2-chloroethylthio)-N'-(3,4-dichlorophenyl)-urea.